US00PP33756P2

(12) United States Plant Patent
Bedford et al.

(10) Patent No.: US PP33,756 P2
(45) Date of Patent: Dec. 21, 2021

(54) APPLE TREE NAMED 'MN80'

(50) Latin Name: *Malus domestica*
Varietal Denomination: MN80

(71) Applicant: Regents of the University of Minnesota, Minneapolis, MN (US)

(72) Inventors: David Bedford, New Germany, MN (US); James Luby, St. Paul, MN (US); Matthew Clark, Hopkins, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 17/152,776

(22) Filed: Jan. 19, 2021

Related U.S. Application Data

(60) Provisional application No. 62/995,353, filed on Jan. 23, 2020.

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 6/7418; A01H 5/08
See application file for complete search history.

*Primary Examiner* — Keith O. Robinson
(74) *Attorney, Agent, or Firm* — Penny J. Aguirre

(57) ABSTRACT

A new cultivar of apple tree named 'MN80' that is characterized by its good winter hardiness in U.S.D.A. Zone 4, its good resistance to apple scab in field observations with multi-gene resistance, its fruit with a long storage life, its fruit with a desirable skin color with a yellow base color and red overcolor, its fruit with a long storage life, and its fruit with a texture that is firm, crisp, and juicy, which is maintained during storage.

2 Drawing Sheets

Botanical classification: *Malus domestica.*
Varietal denomination: 'MN80'.

BACKGROUND OF THE INVENTION

The present invention relates to a new and distinct cultivar of apple tree, botanically known as *Malus domestica* 'MN80', referred to hereafter by its cultivar name, 'MN80'. 'MN80' is a new cultivar of apple tree for use in commercial apple production and home gardens.

The new apple tree arose from a cross made in 1990 between 'Honeycrisp' (U.S. Plant Pat. No. 7,197) as the female parent and 'Liberty' (not patented) as the male parent. The Inventors selected 'MN80' as a single unique tree amongst the seedlings from the above cross in 2004 in Excelsior, Minn.

Asexual propagation of the new cultivar was first accomplished by bud grafting in 2005 under the direction of the Inventors in Excelsior, Minn. Asexual propagation by bud grafting has determined that the characteristics of the new cultivar are stable and are reproduced true to type in successive generations.

SUMMARY OF THE INVENTION

The following traits have been repeatedly observed and represent the characteristics of the new cultivar and distinguish 'MN80' as a unique cultivar of apple tree.

1. 'MN80' exhibits good winter hardiness at least U.S.D.A. hardiness Zone 4.
2. 'MN80' exhibits good resistance to apple scab in field observations with multi-gene resistance.
3. 'MN80' exhibits fruit with a long storage life.

4. 'MN80' exhibits fruit with a desirable skin color with a yellow base color and red overcolor.
5. 'MN80' exhibits fruit with a texture that is firm, crisp, and juicy, which is maintained during storage.

'Honeycrisp', the female parent of 'MN80', differs from 'MN80' in having less apple scab resistance, a less dense and firm fruit texture, and slightly earlier fruit ripening. 'Liberty', the male parent of 'MN80', differs from 'MN80' in having single gene apple scab resistance, and in having fruit that is less juicy.

BRIEF DESCRIPTION OF THE DRAWINGS

The accompanying color photograph was taken of 'MN80' trees 12 years in age that were grown in a trial plot in Excelsior, Minn.

The photograph in FIG. 1 provides a view of the fruit of 'MN80'.

Figure 1:
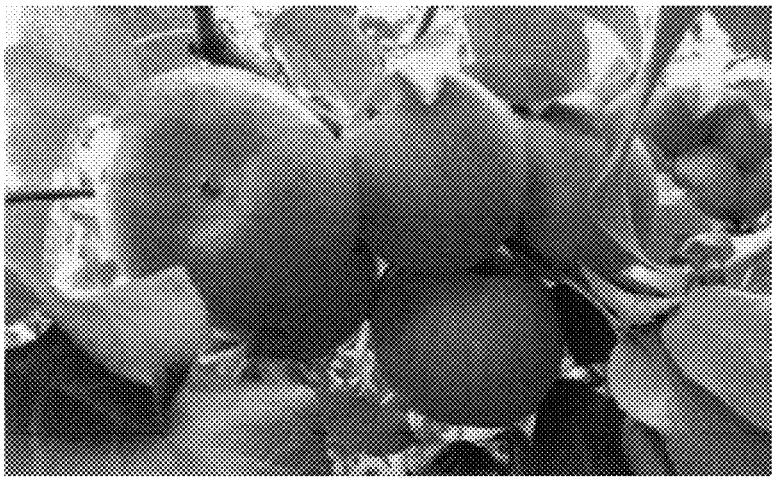
Figure 2:
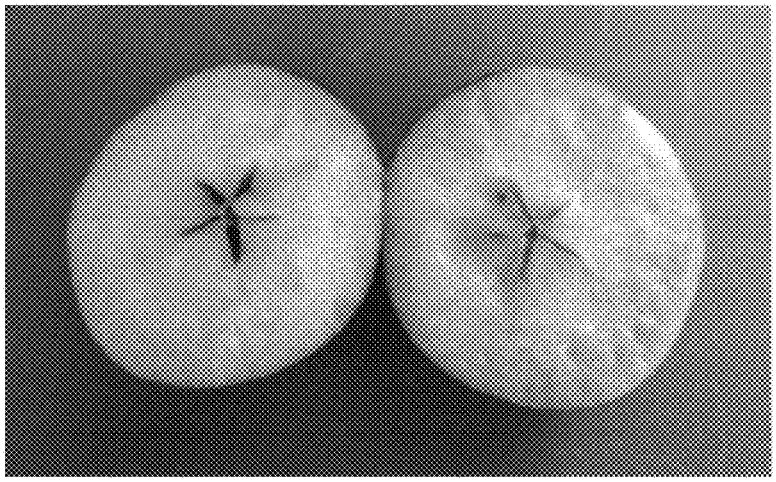

The photograph in FIG. 2 provides a view of the fruit flesh of 'MN80'.

Figure 3:
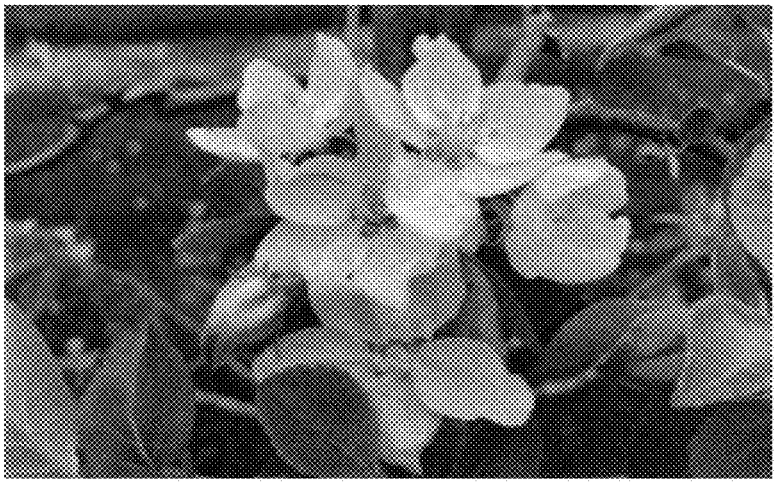

The photograph in FIG. 3 provides a view of the flowers of 'MN80'.

Figure 4:
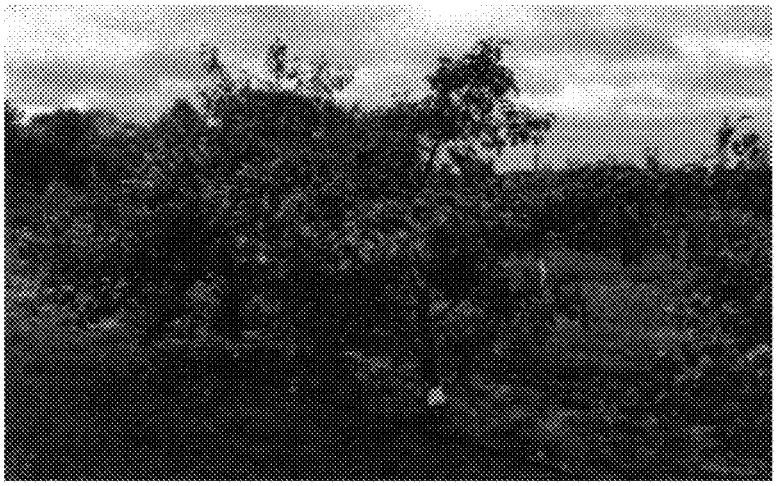

The photograph in FIG. 4 provides a view of the tree habit of 'MN80'.

The colors in the photograph are as close as possible with the photographic and printing technology utilized and the color values cited in the detailed botanical description accurately describe the colors of the new apple tree.

DETAILED BOTANICAL DESCRIPTION

The following is a detailed description of the new apple variety as observed on trees 12 years in age as grown in a trial field in Excelsior, Minn. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

Tree description:

*Tree habit.*—Spreading and rounded.

*Tree size.*—An average of 3 m in height and spread as a 12-year-old tree.

*Growth rate.*—Moderate.

*Disease resistance.*—Has has exhibited good resistance to apple scab (*Venturia inaequalis*) in field observations and following inoculation in the greenhouse, genetic testing indicates it has markers linked to genes from both parents that are known to confer resistance.

*Cold hardiness.*—At least in U.S.D.A. Zone 4.

*Branching habit.*—Spreading.

*Branch frequency.*—Medium.

*Branch strength.*—Strong.

*Branch angle.*—45° to 90°.

*Predominance of bearing.*—Both spurs and shoots.

*Trunk diameter.*—Average of 9 cm in width 30 cm in height from the soil level.

*Branches.*—Average of 11 primary lateral branches; average of 1.3 m in length and 3 cm in width at mid branch, held at an angle of 45° to 90° average of 7 secondary branches per primary branch; average of 50 cm in length and 1 cm in width, held horizontal to primary branches.

*Trunk color.*—Blend of N199A and N199C.

*Trunk surface.*—Medium-barked.

Description of dormant shoots:

*Pubescence on upper one-year-old shoot.*—Varies from weak to heavy.

*Shine of bark.*—Medium.

*Thickness of shoot at center of middle internode.*—Average of 3.8 mm.

*Internode length.*—Average of 1.9 cm.

*Bark color* (*using bark on* 1-*year-old shoots exposed to sun*).—A color between 183A and 166A.

3-*year-old wood.*—Blend of N199B and N199C in color, surface satiny with areas of fine bark 156B in color, lenticels; average of 2 mm in length and 0.7 mm in width, average of 12 per 1.5 sq. cm, 156C in color.

*Shoot angle.*—Approximately 45°.

*Lenticels.*—Average of 1 mm in length and 0.5 mm in width), linear-oblong in shape, approximately 20 per shoot 3 cm in length and 3 cm in width, 156B in color.

Description of growing shoots:

*Color of growing tip of shoot.*—166A and 166B.

*Shape of shoot tip leaves in cross section.*—Concave.

*Pubescence of shoot tip leaves.*—High on outer surface of leaf and moderate on lower surface.

*Color of shoot tip leaves.*—194C on outer surface and blend of 138B and 138C on inner surface.

*Distribution of color other than green on shoot tip leaves.*—None.

Leaf description:

*Leaf orientation.*—Outward to upward.

*Leaf division.*—Simple.

*Leaf shape.*—Ovate-elliptic.

*Leaf size.*—Average of 8.9 cm in length and 6 cm in width.

*Leaf apex.*—Young; rounded to obtuse, mature; acute to cuspidate.

*Leaf base.*—Rounded to slightly cordate.

*Leaf surface.*—Young leaves; before expanding both surfaces are densely covered with short woolly puberulent hairs, when young slightly satiny and sparsely pubescent on upper surface and dull with dense pubescence on lower surface, mature leaves upper surface; glossy, glabrous except main vein which is densely covered with woolly pubescence which matches vein color, mature leaves lower surface; dull and densely covered in lanate pubescence that matches vein color, soft to the touch.

*Leaf aspect.*—slightly concave with apex recurved.

*Leaf margin.*—Serrate and more crenate on lower part of leaf.

*Leaf color.*—Young leaves (before expanding); 194C on outer surface and a blend of 138B and 138C on inner surface, young leaves; 138A on upper surface and 138B on lower surface, mature leaves; upper surface; 143A, main vein 145D and flushed with 184A, mature leaves lower surface; a blend of 198A and 196C, veins NN155D and 158C.

*Leaf venation.*—Pinnate main veins with netted minor veins.

*Leaf bud.*—Average of 4 mm in length and 3.5 mm in width, satiny and flaky surface, 183B, flushed with 196B at the tip.

*Petiole.*—Average of 3.5 cm in length and 1 mm in diameter, 145C and flushed with 196B, surface densely covered with lanate pubescence matching leaf surface color, slightly pendulant.

*Stipules.*—Small in size, 2 mm in length and 144A and flushed with 196B in color at apex, acute apex, base fused.

Flower description:

*Beginning flowering date.*—Typically from May 13th to May 20th in Excelsior, Minn.

*Number of flowers.*—Typically 5 to 6 per spur.

*Inflorescence type.*—Cluster, slightly corymb-like.

*Inflorescence size.*—An average of 7.2 cm in diameter and 4.5 cm in depth.

*Flower buds.*—Globose in shape, an average of 1.3 cm in length and diameter, color; a blend of 68A, 68B and NN155C with sepal portion 138B, surface is glabrous with sepal portion pubescent.

*Flower size.*—Average of 4.7 cm in diameter and 1.4 cm in depth.

*Flower fragrance.*—Pleasant, moderate, rose-like fragrance.

*Flower aspect.*—Upright to outward facing.

*Petals.*—5 per flower, un-fused, lower ⅓ overlapping, broad ovate in shape, broadly acute to obtuse apex, entire and slightly undulate margin, base cuneate-truncate with very base apiculate into sepal, aspect slightly concave with tips held upright, an average of 2 cm in length and 1.6 cm in width at widest point and 6 mm in width at narrowest point, surface texture upper and lower surface glabrous and satiny, color: upper surface color when opening and fully open;

NN155C slightly suffused with 75A lower surface when opening and fully open; NN155C irregularly suffused with 75A.

*Sepals.*—5, free lobes; lanceolate in shape, entire margin, acuminate apex, fused base into cup-like base, lobes an average of 6 mm in length and 3.5 mm in width (at base), base an average of 4 mm in length and 3.5 mm in width, both surfaces are densely covered with woolly matted puberulent hairs NN155B in color, <0.3 mm in length, both surfaces under the pubescence is satiny, color young upper and lower surfaces opening and mature 138B with very tip 183A.

*Pedicel.*—Average of 2 cm in length and 1.8 mm in width, held upright to outward, moderately strong, surface densely covered with woolly matted puberulent hairs <0.5 mm in length, 144A with pubescence NN155B in color.

*Bracts.*—1 to 2 at base of pedicel, linear in shape, an average of 2 mm in length and 0.75 mm in width, 138A in color on both surfaces and quickly drying, pubescent on both surfaces.

*Pistil.*—1, with 5 styles, 1.2 cm in length, style; 8 mm in length and 0.5 mm in width, 144B in color, stigma; angled and rounded, 151B in color, ovary; 4 mm in length and 2.5 mm in width, N137A in color.

*Stamens.*—Average of 18, anther; bi-fid, slightly curved, 2 mm in width, 1.5 mm in length, 4D in color, pollen minimal in quantity and too little for color reading, filament; 8 mm in length and 0.7 mm in width, 144D in color, nectar; not observed.

*Pollination requirements.*—Self incompatible.

Fruit description:

*Fruit size.*—Medium, average of 7.2 cm in width and 5.5 cm in height.

*Position of maximum diameter.*—Slightly above the midway point between proximal and distal ends.

*Fruit shape.*—Globose.

*Fruit symmetry.*—Asymmetrical.

*Fruit prominence of ribbing.*—Absent to weak.

*Size of eye (calyx).*—5.4 mm in diameter.

*Persistence of calyx.*—Present.

*Length of sepal.*—3.2 mm.

*Spacing of sepals at base.*—Touching to overlapping.

*Depth of eye basin.*—4 mm.

*Width of eye basin.*—Average of 2.1 cm.

*Thickness of stalk.*—Medium.

*Stalk size.*—Average of 2 mm in width and in 1.9 cm length.

*Depth of stalk cavity.*—Ranges from 1.1 cm to 1.4 cm.

*Width of stalk cavity.*—Average of 1.8 cm.

*Relief of surface.*—Slightly hammered.

*Bloom of skin.*—Moderate to heavy.

*Waxiness of skin.*—Slight.

*Thickness of skin.*—Medium.

*Skin color.*—75 to 85% covered with a blend of 46A and 46B over a background color of 11B.

*Presence of russet.*—Low, positioned around the stalk cavity.

*Lenticels.*—Medium (average of 0.6 mm), moderately prominent.

*Color of flesh.*—A blend of 11C and 11D.

*Distinctness of core line.*—Weak.

*Aperture of locules.*—Closed.

*Fruit set.*—Intermediate to good.

*Fruit maturity date.*—Medium to late, typically September 20th to September 30th in central Minnesota.

*Seed.*—A blend of 200C and 165A in color, deltoid in shape, an average of 9 mm in length and 4 mm in diameter.

*Browning of flesh.*—Weak to medium.

*Firmness (without skin).*—Firm, 18.2 to 21.1 lbs. at harvest.

*Texture of flesh.*—Firm to crisp.

*Cropping frequency.*—Annual.

*Fruit flavor.*—Somewhat acidic when harvested early but well balanced at full maturity.

*Fruit weight.*—Average of 205 g (observed on 12-year-old trees grown in Excelsior, Minn.).

*Fruit productivity.*—Moderate.

*Juiciness.*—Medium.

*Acidity.*—Moderate.

*Brix.*—Average of 15.8°.

*Storage life.*—150 to 230 days in ambient atmosphere storage (average temperature of 34° F.).

*Market use.*—Fresh Fruit.

It is claimed:

1. A new and distinct variety of apple tree named 'MN80' as herein illustrated and described.

* * * * *